US012778501B2

(12) United States Patent
Machado Gamboa et al.

(10) Patent No.: US 12,778,501 B2
(45) Date of Patent: Nov. 3, 2026

(54) MEDICAL SYSTEM WITH PHYSIOLOGICAL SENSORS

(71) Applicant: Medidata Solutions, Inc., New York, NY (US)

(72) Inventors: Kevin Machado Gamboa, New York, NY (US); Melissa Ceruolo, New York, NY (US)

(73) Assignee: Medidata Solutions, Inc., New York, NY (US)

( * ) Notice: Subject to any disclaimer, the term of this patent is extended or adjusted under 35 U.S.C. 154(b) by 275 days.

(21) Appl. No.: 18/655,427

(22) Filed: May 6, 2024

(65) Prior Publication Data

US 2025/0339095 A1 Nov. 6, 2025

(51) Int. Cl.

| | |
|---|---|
| ***A61B 5/00*** | (2006.01) |
| ***A61B 5/0205*** | (2006.01) |
| ***A61B 5/024*** | (2006.01) |
| ***A61B 5/11*** | (2006.01) |
| ***G16H 40/67*** | (2018.01) |

(52) U.S. Cl.

CPC ............ *A61B 5/486* (2013.01); *A61B 5/0205* (2013.01); *A61B 5/1118* (2013.01); *A61B 5/742* (2013.01); *A61B 5/746* (2013.01); *G16H 40/67* (2018.01); *A61B 5/02438* (2013.01); *A61B 5/4815* (2013.01); *A61B 2562/0219* (2013.01)

(58) Field of Classification Search

None

See application file for complete search history.

(56) References Cited

U.S. PATENT DOCUMENTS

| | | | | |
|---|---|---|---|---|
| 5,474,079 | A * | 12/1995 | Brodnick | A61B 5/336 600/524 |
| 7,254,440 | B1 * | 8/2007 | Kroll | A61B 5/349 600/517 |
| 10,827,973 | B1 * | 11/2020 | Alzamzmi | G16H 50/70 |
| 11,158,407 | B2 * | 10/2021 | Ohnemus | G16H 10/60 |
| 2012/0232414 | A1 * | 9/2012 | Mollicone | A61B 5/024 600/508 |
| 2013/0005310 | A1 * | 1/2013 | Lim | H04M 1/72454 455/414.1 |
| 2014/0005947 | A1 * | 1/2014 | Jeon | A61B 5/7278 702/19 |

(Continued)

OTHER PUBLICATIONS

Extended European Search Report in European Appln. No. 25174615.2, mailed on Oct. 6, 2025, 9 pages.

(Continued)

*Primary Examiner* — Manolis Pahakis

(74) *Attorney, Agent, or Firm* — Fish & Richardson P.C.

(57) ABSTRACT

In an example method, a computer system receives, from a wearable medical sensor, acceleration data indicating physical activity of a subject, activity classification data, sleep data, and one or more vital sign metrics. The system determines a physical activity score, a sleep score, and a vital signs score based on the acceleration data, the activity classification data, the sleep data, and the one or more vital sign metrics. The system determines a quality of life score for the subject based on the physical activity score, the sleep score, and the vital signs score. The system causes the quality of life score to be presented to the subject using a display screen.

25 Claims, 10 Drawing Sheets

(56) References Cited

U.S. PATENT DOCUMENTS

| | | | | |
|---|---|---|---|---|
| 2014/0085077 | A1* | 3/2014 | Luna | A61B 5/0205<br>340/539.11 |
| 2016/0270717 | A1* | 9/2016 | Luna | A61B 5/743 |
| 2017/0147775 | A1* | 5/2017 | Ohnemus | G16H 50/50 |
| 2018/0107943 | A1* | 4/2018 | White | G06N 5/01 |
| 2018/0247713 | A1 | 8/2018 | Rothman | |
| 2019/0115107 | A1* | 4/2019 | Hong | A61B 5/002 |
| 2022/0015695 | A1* | 1/2022 | Margarito | A61B 5/4809 |
| 2022/0027783 | A1* | 1/2022 | Neumann | G06F 16/2433 |
| 2022/0110547 | A1 | 4/2022 | Kinnunen et al. | |
| 2022/0151569 | A1* | 5/2022 | Reifman | A61B 5/02405 |
| 2022/0304622 | A1* | 9/2022 | Freckleton | A61B 5/4815 |
| 2022/0310264 | A1* | 9/2022 | Kaput | G16H 20/10 |
| 2023/0065695 | A1* | 3/2023 | Singleton | G16H 40/63 |
| 2023/0148956 | A1* | 5/2023 | Narayanan | A61B 5/4809<br>600/301 |
| 2023/0245780 | A1 | 8/2023 | Molony et al. | |
| 2023/0248285 | A1* | 8/2023 | Abdel-Ghaffar | A61B 5/0205<br>600/301 |
| 2023/0263441 | A1* | 8/2023 | Sheth | A61B 5/1128<br>340/539.12 |
| 2023/0343459 | A1* | 10/2023 | Prozorovscaia | G16H 50/30 |
| 2024/0131338 | A1* | 4/2024 | Straka | A61N 1/36078 |
| 2024/0194344 | A1* | 6/2024 | Capodilupo | A61B 5/0205 |
| 2025/0140420 | A1* | 5/2025 | Mukherjee | G16H 50/30 |

OTHER PUBLICATIONS

Blome et al., "Measuring Change in Quality of Life: Bias in Prospective and Retrospective Evaluation," Value in Health, 2015, 18:110-115.

Brannan et al., "10 minutes brisk walking each day in mid-life for health benefits and towards achieving physical activity recommendations Evidence summary," Public Health England, Aug. 2017, 17 pages.

Bull et al., "World Health Organization 2020 guidelines on physical activity and sedentary behaviour," Br. J. Sports Med., Dec. 2020, 54(24):1451-1462.

Buysse et al., "The Pittsburgh Sleep Quality Index: a new instrument for psychiatric practice and research," Psychiatry Research, May 1989, 28(2):193-213.

Cruz et al., "Prospective Associations of Daily Step Counts and Intensity With Cancer and Cardiovascular Disease Incidence and Mortality and All-Cause Mortality," JAMA Intern Med., Sep. 12, 2022, 182(11):1139-1148.

Evenson et al., "Objective Measurement of Physical Activity and Sedentary Behavior Among US Adults Aged 60 Years or Older," Prev. Chronic Dis., Dec. 15, 2011, vol. 9, pp. 1-10.

Katzmarzyk et al., "Sedentary Behavior and Health: Update from the 2018 Physical Activity Guidelines Advisory Committee," Medicine & Science in Sports & Exercise, Jun. 2019, 51(6):1227-1241.

Murtagh et al., "The effect of walking on risk factors for cardiovascular disease: an updated systematic review and meta-analysis of randomised control trials," Preventive Medicine, Mar. 2015, 72:34-43.

Oja et al., "Physical activity recommendations for public health: development and policy context," EPMA Journal, Jun. 8, 2011, 2:253-259.

Owen et al., "Too Much Sitting: The Population-Health Science of Sedentary Behavior," Exerc Sport Sci Rev., Jul. 2010, 38(3):105-113.

Park et al., "Sedentary Lifestyle: Overview of Updated Evidence of Potential Health Risks," Korean J Fam Med., Nov. 19, 2020, 41(6):365-373.

Streiner et al., "Chapter 6—Biases in responding," Health Measurement Scales: A practical guide to their development and use, Sep. 2008, pp. 100-130, Abstract Only.

Tempelaar et al., "Subjective data, objective data and the role of bias in predictive modelling: Lessons from a dispositional learning analytics application," PLoS One, Jun. 12, 2020, 29 pages.

Tudor-Locke et al., "Walking cadence (steps/min) and intensity in 41 to 60-year-old adults: the Cadence-adults study," International Journal of Behavioral Nutrition and Physical Activity, Nov. 10, 2020, 17(137):1-10.

Wulfovich et al., "Chapter 1 Unfolding the Quantification of Quality of Life," Quantifying Quality of Life, Apr. 14, 2022, pp. 3-24.

Zhang et al., "Resting heart rate and all-cause and cardiovascular mortality in the general population: a meta-analysis," CMAJ, Feb. 16, 2016, 188(3):E53-E63.

* cited by examiner

MEDICAL SYSTEM WITH PHYSIOLOGICAL SENSORS

TECHNICAL FIELD

This description generally relates to a medical system with physiological sensors.

BACKGROUND

In general, a user's health related quality of life can be assessed by measuring one or more physiological characteristics of the user and comparing the measured physiological characteristics to a health reference. For example, a user having physiological characteristics that meet or exceed a particular health reference may have a high quality of life, whereas a user having physiological characteristics that do not meet the health reference may have a low quality of life.

SUMMARY

In general, a wearable medical system can be used to monitor a user's health related quality of life and to facilitate treatment of the user.

In an example implementation, a medical monitoring system includes a sensor apparatus configured to obtain sensor data representing one or more physiological characteristics of a user, and one or more processor modules (e.g., computer processors) configured to process the sensor data and determine one or more metrics representing aspects of the user's physical health related quality of life.

For instance, the medical monitoring system can obtain sensor data indicating a physical activity level, sleep metrics, and/or vital signs of the user. For example, the sensor data can include measurements of the user's physical activity such as the number of steps taken during a period of time, and/or cardiac activity, such as the user's heart rate or pulse rate (e.g., obtained by one or more cardiac sensors) during the period of time. Further the sensor data can include measurements of the user's movements (e.g., acceleration data obtained using one or more acceleration sensors) during the period of time. Based on these measurements, the medical monitoring system can determine a metric that represents the user's physical health related quality of life. Further, the medical monitoring system can present the metric to the user or another user (e.g., a health care provider) to facilitate treatment of the user and/or monitoring of the user's health over time.

The implementations described herein can provide various technical benefits. As an example, the implementations described herein allow a computer system to automatically determine a user's physical health related quality of life based on sensor data (e.g., cardiac data, acceleration data, etc.), without requiring manual feedback from a human. Further, the medical monitoring system can provide this functionality by performing computer-specific operations on input data in an objective manner (and in a manner that is not feasible for a human to perform), rather than relying on a human interpretation of the input data which may be less suitable for performance by a computer.

As another example, the implementations described herein can be used to facilitate monitoring and treatment of a user (e.g., during a clinical trial of a pharmaceutical composition or other intervention), thereby improving the user's physical health related quality of life and/or health. For example, a medical monitoring system can generate a metric representing the user's physical health related quality of life and provide the metric to the user or another user (e.g., a health care provider). The physical health related quality of life metric determined by the medical monitoring system can provide an objective measure of a user's physical health related quality of life to reduce variability and bias from subjective user responses to questionnaires or surveys, for example. Based on this information, the user or other user can take active steps to improve the user's physical health related quality of life, such as conducting further tests to diagnose the user's medical condition, changing the user's behavior, lifestyle, and/or diet, or any other action.

In an aspect, a method includes receiving, from a wearable medical sensor, acceleration data indicating physical activity of a subject, activity classification data, sleep data, and one or more vital sign metrics; determining a physical activity score, a sleep score, and a vital signs score based on the acceleration data, the activity classification data, the sleep data, and the one or more vital sign metrics; determining a quality of life score for the subject based on the physical activity score, the sleep score, and the vital signs score; and causing the quality of life score to be presented to the subject using a display screen.

Implementations of this aspects can include one or more of the following features.

Some implementations include storing a data structure representing the quality of life score on a hardware storage device.

Some implementations include determining that the quality of life score is less than a threshold quality of life score; and in response to determining that the quality of life score is less than the threshold quality of life score, causing an alert to be generated indicating that the quality of life score is less than the threshold quality of life score.

Some implementations include determining a plurality of quality of life scores for the subject at a plurality of times; and determining a variability in quality of life for the subject based on the plurality of quality of life scores.

Some implementations include determining a baseline quality of life for the subject based on the plurality of quality of life scores; determining one or more subsequent quality of life scores after determining the baseline quality of life; and determining that the one or more subsequent quality of life scores deviates more than a threshold amount from the baseline quality of life.

In some implementations, the vital sign sensor includes at least one of a heart rate sensor or a pulse rate sensor.

Some implementations include receiving heart rate data and data specifying a steps count from the wearable medical sensor, where the vital signs score is determined based on the heart rate data, the steps count, and the activity classification data.

In some implementations, determining the vital signs score includes receiving sleep metrics from the wearable medical sensor; determining a resting while awake vitals score based on the activity classification data, the acceleration data, and the heart rate data; determining a sleeping vitals score based on the activity classification data, the acceleration data, the sleep metrics, and the heart rate data; determining a walking vitals score based on the activity classification data, the acceleration data, the steps count and the heart rate data; and determining the vital signs score based on the resting while awake vitals score, the sleeping vitals score, and the walking vitals score.

In some implementations, determining the physical activity score includes determining a walking score and a sedentary score.

Some implementations include receiving data specifying a steps count from the wearable medical sensor, where the walking score is determined based on the steps count, the acceleration data, and the activity classification data; and the sedentary score is determined based on the activity classification data and an activity count based on the acceleration data.

In some implementations, the activity count represents movement of the subject determined based on a magnitude of the acceleration over a time interval.

Some implementations include filtering the activity classification data to extract low activity samples while the subject is awake, where the sedentary score includes a count of continuous low activity samples while the subject is awake.

In some implementations, the walking score includes a step count score, a purposeful walk score, a light walk score, a moderate walk score, and a vigorous walk score, where each of the purposeful walk score, the light walk score, the moderate walk score, and the vigorous walk score is determined based on a number of steps in a time interval.

In some implementations, determining the sleep score includes determining one or more of a sleep duration score, a sleep latency score, and a sleep efficiency score based on the sleep metrics.

Some implementations include determining, based on the quality of life score, one or more recommendations for improving a health of the subject, and causing the one or more recommendations to be presented to the subject.

Some implementations include monitoring the subject based on the quality of life score.

Other embodiments of this aspect include corresponding computer systems, apparatuses, and computer programs recorded on one or more computer storage devices, each configured to perform the actions or operations described herein. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by a data processing apparatus, cause the apparatus to perform the actions.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
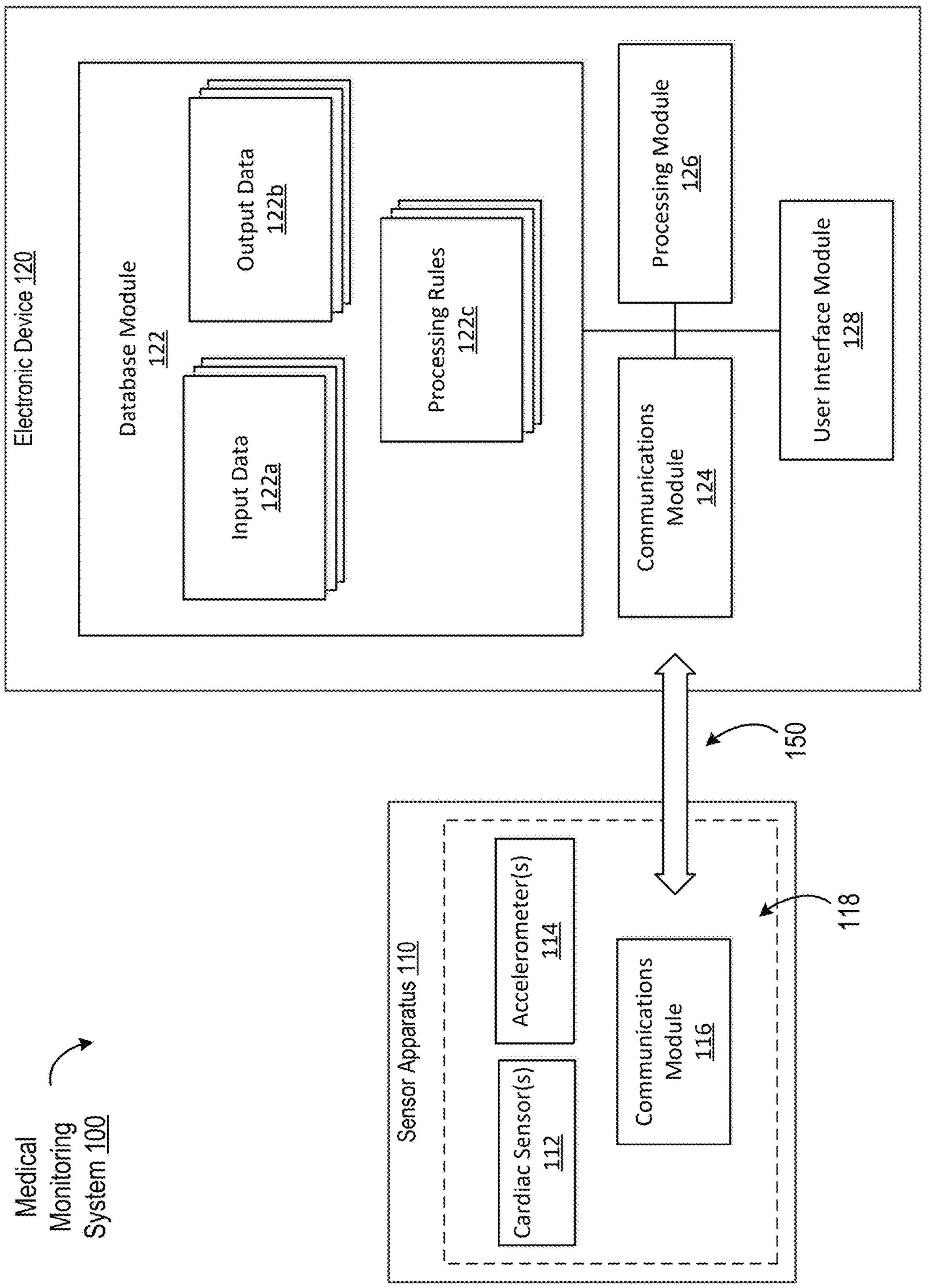
FIG. 1 is a diagram of an example medical monitoring system.

FIG. 1 shows an example medical monitoring system 100 for automatically monitoring the physical health related quality of life of a user. The medical monitoring system 100 includes a sensor apparatus 110 and an electronic device 120 that are communicatively coupled to one another (e.g., via one or more wired or wireless communications links 150). In general, the medical monitoring system 100 obtains sensor data regarding a user using the sensor apparatus 110, and processes the sensor data using the electronic device 120 to determine one or more scores representing the user's health condition. The one or more scores can represent the user's health condition based on a health reference.

The sensor apparatus 110 includes one or more sensors configured to obtain measurements regarding a physiology of the user, a physical behavior of the user (e.g., physical activity, sleep patterns), and/or any other characteristics of the user.

For example, as shown in FIG. 1, the sensor apparatus 110 can include one or more accelerometers 114 configured to obtain sensor data representing a movement or motion of the user in one or more directions. For example, at least some of the accelerometers 114 can be tri-axis accelerometers that are configured to measure acceleration in three directions (e.g., the x-direction, the y-direction, and the z-direction on a Cartesian coordinate system). In some implementations, the accelerometers 114 can obtain sensor data at 32 Hz (or approximately 32 Hz).

Further, the sensor apparatus 110 can include one or more cardiac sensors 112 configured to obtain sensor data representing the cardiac activity of a user. In some implementations, the cardiac sensor(s) 112 can include one or more electrocardiogram (ECG) sensors and/or one or more photoplethysmography (PPG) sensors. In some implementations, the cardiac sensors 112 can obtain sensor data at 64 Hz or more, 125 Hz or more, or up to 250 Hz (or approximately 250 Hz).

Further, the sensor apparatus 110 includes a communications module 116 configured to transmit data and/or receive data from the electronic device 120. As an example, the communications module 116 can include one or more receivers, transmitters, and/or transceivers. In some implementations, the communications module 116 can communicate with the electronic device 120 via one or more wireless links (e.g., serial links, Ethernet links, etc.) and/or wireless links (e.g., Wi-Fi links, Bluetooth links, etc.).

Further, the sensor apparatus 110 is configured to be worn by a user. For example, as shown in FIG. 1, the sensor apparatus 110 can include a substrate 118 that is configured to be affixed to the user's body (e.g., via an adhesive or a strap). Further, the cardiac sensors 112, accelerometer 114, and communications module 116 can be attached to the substrate, such that they are secured to the user's body. In some implementations, at least a portion of the substrate 118 can be composed of compliant materials such as silicone, rubber, elastomers, and/or any other flexible material. In some implementations, at least a portion of the compliant substrate 118 can be composed of rigid materials such as rigid metals, rigid plastics, etc.

In general, the electronic device 120 is configured to receive sensor data obtained by the sensor apparatus 110, and process the sensor data to determine one or more metrics representing the user's health condition. Further, the electronic device is configured to present information regarding the scores and any other information to the user and/or another user (e.g., a health care provider).

In general, the electronic device 120 can include any number of devices that are configured to receive, process, and transmit data. Examples of the electronic device 120 include client computing devices (e.g., desktop computers or notebook computers), server computing devices (e.g., server computers or cloud computing systems), mobile computing devices (e.g., cellular phones, smartphones, tablets, personal data assistants, notebook computers with networking capability), wearable computing devices (e.g., smart phones or headsets), and other computing devices capable of receiving, processing, and transmitting data. In some implementations, the electronic device 120 can include computing devices that operate using one or more operating systems (e.g., Microsoft Windows, Apple macOS, Linux, Unix, Google Android, and Apple IOS, among others) and one or more architectures (e.g., x86, PowerPC, and ARM, among others).

In FIG. 1, the electronic device 120 is illustrated as a single component. However, in practice, the electronic device 120 can be implemented on one or more computing devices (e.g., each computing device including at least one processor such as a microprocessor or microcontroller). As an example, the electronic device 120 can be a single computing device, such as a single smartphone. As another example, the electronic device 120 can include multiple computing devices that are connected via a network (e.g., the Internet, local area network, etc.), and the components of the electronic device 120 can be maintained and operated on some or all of the computing devices. For instance, electronic device 120 can include several computing devices, and the components of the electronic device 120 can be distributed on one or more of these computing devices.

As shown in FIG. 1, the electronic device 120 includes a database module 122, a communications module 124, a processing module 126, and a user interface module 128. The operation modules can be provided as one or more computer executable software modules, hardware modules, or a combination thereof. For example, one or more of the operation modules can be implemented as blocks of software code with instructions that cause one or more processors to execute operations described herein. In addition, or alternatively, one or more of the operation modules can be implemented in electronic circuitry such as, e.g., programmable logic circuits, field programmable logic arrays (FPGA), or application specific integrated circuits (ASIC).

The communications module 124 is configured to transmit data and/or receive data from the sensor apparatus 110. As an example, the communications module 124 can include one or more receivers, transmitters, and/or transceivers. In some implementations, the communications module 124 can communicate with the sensor apparatus 110 (e.g., via the communication module 116) via one or more wireless links (e.g., serial links, Ethernet links, etc.) and/or wireless links (e.g., Wi-Fi links, Bluetooth links, etc.).

The database module 122 maintains information related to the operation of the medical monitoring system 100.

As an example, the database module 122 can store input data 122*a* that is used for determining one or more metrics representing a health of a user. For instance, the input data 122*a* can include at least some of the sensor data generated by the sensor apparatus 110 (e.g., cardiac data, acceleration data, etc.).

As another example, the database module 122 can store output data 122*b* generated by electronic device 120. As an example, the output data 122*b* can include one or more metrics generated by the electronic device 120 based on the input data 122*a*.

Further, the database module 122 can store processing rules 122*c* specifying how data in the database module 122 can be processed to perform the operations described herein.

As an example, the processing rules 122*c* can include one or more rules that specify how the input data 122*a* is formatted, parsed, and processed to determine one or more corresponding metrics or scores regarding a user.

As another example, the processing rules 122*c* can include one or more rules that specify the conditions in which data is presented to a user (e.g., using the user interface module 128), and the manner in which the data is presented.

As another example, the processing rules 122*c* can include one or more rules that specify the manner in which data is stored for future retrieval and/or processing (e.g., using the database module 122).

Example data processing techniques are described in further detail below.

The processing module 126 processes data stored or otherwise accessible to the electronic device 120. For instance, the processing module 126 can be used to execute one or more of the operations described herein (e.g., by executing the processing rules 122*c* with respect to the input data 112*a* in order to generate the output data 122*b*).

The user interface module 128 is configured to present information to a user and/or to receive inputs from a user. As an example, the user interface module 128 can include one more display devices (e.g., display screens, touch screens, etc.) that are configured to present a user interface (e.g., graphical user interface, GUI) that enables users to interact with the electronic device 120 and/or the sensor apparatus 110. Example interactions include viewing data, transmitting data from one component to another, and/or issuing commands to the electronic device 120 and/or sensor apparatus 110. Commands can include, for example, any user instruction to one or more of the electronic device 120 and/or sensor apparatus 110 to perform particular operations or tasks. In some implementations, the user inter-face module can also present information to a user aurally (e.g., using one or more speakers) and/or via haptic feedback (e.g., using one or more haptic generators, such as a vibration generation).

In some implementations, a software application can be used to facilitate performance of the tasks described herein. As an example, an application can be installed on the electronic device 120. Further, a user can interact with the application to input data and/or commands to the electronic device 120, and review data generated by the electronic device 120.

Figure 2:
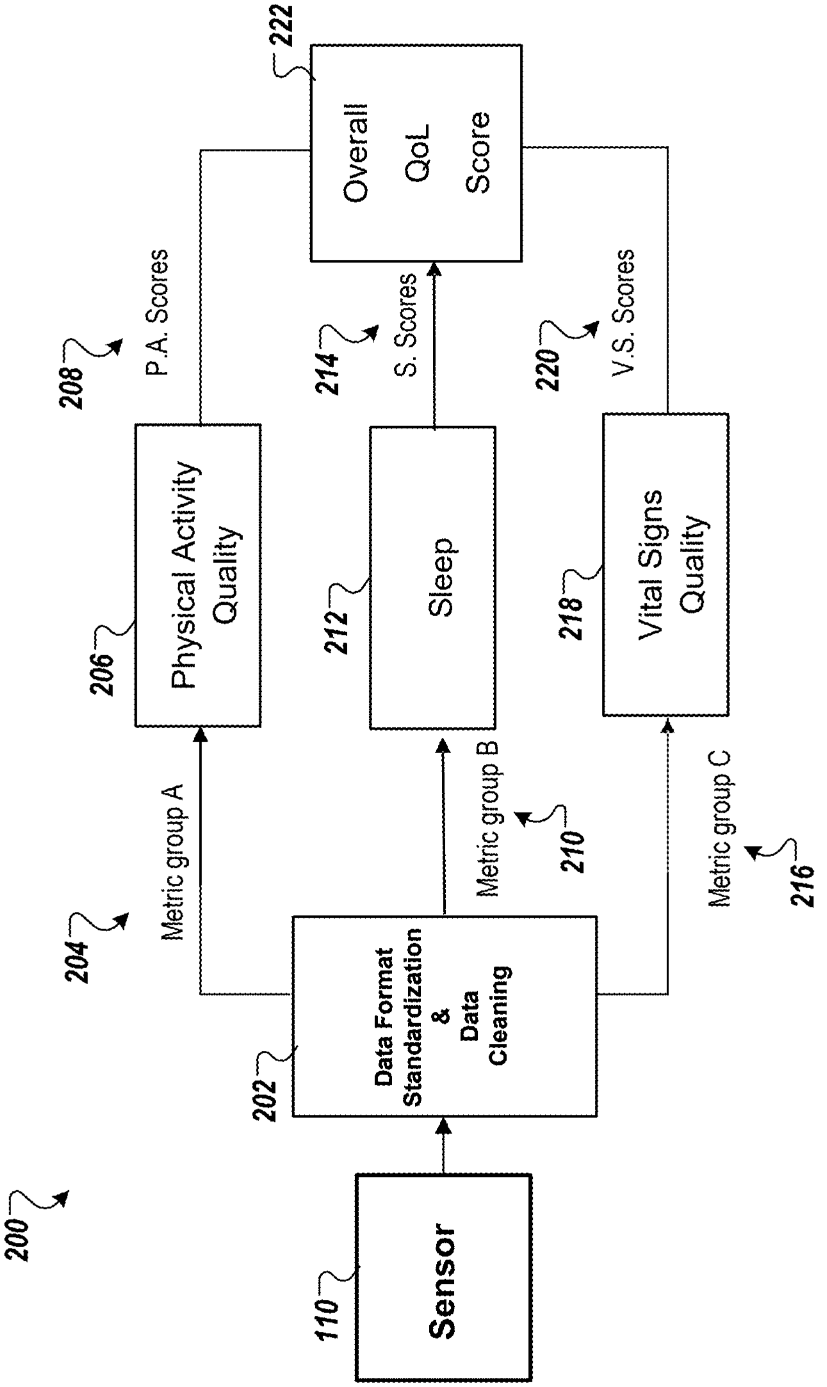
FIG. 2 is a flow chart diagram of an example method of using a medical monitoring system to determine a physical health related quality of life score for a user.

FIG. 2 illustrates an example method 200 of determining a user's physical health-related quality of life using the medical monitoring system 100.

In this example, the sensor apparatus 110 is worn by a user (e.g., affixed to the user's skin or secured to the user's wrist). The sensor apparatus 110 measures physiological characteristics of the user while the user is wearing the sensor apparatus 110. Physiological characteristics can include data that indicates a physical health of the user such as acceleration data, activity classifications, vital sign measurements, step counts, sleep status, sleep patterns, heart rate, etc. For example, the sensor apparatus 110 continuously obtains measurements of the physiological characteristics of the user while the user is wearing the sensor apparatus 110.

The sensor apparatus 110 outputs the measured data to a standardized data format and data cleaning module 202. The standardized data format and data cleaning module 202 is, for example, included in the electronic device 120. In the standardized data format and data cleaning module 202, the measured data from the sensor apparatus 110 is formatted into a common format for use in determining the health-related quality of life score for the user. For example, sensor metric standardization converts each particular sensor data type, column names and sample frequency resolution into a standardized data format. Using a standardized data format enables data obtained from multiple sensors and/or sensor types to be processed in a consistent manner. The data cleaning portion of the module 202 includes to correcting data errors, removing noise, handling (e.g., removing) data outliers, and determining that the data is suitable for further analysis. The module 202 can, for example, determine that the data is suitable for further analysis based on a number of samples per day available in the data and/or irregular values per unit of time (e.g., too high or too low of a value per unit time). The module 202 can also generate a log of the data cleaning activities, including the actions taken and any issues encountered. This log can be used to generate a report that summarizes the data cleaning process and its outcomes.

The module 202 outputs the formatted and cleaned data in subsets (e.g., metric groups) to multiple quality of life scoring blocks. For example, in each quality of life scoring block a normalized score with a value in the range of 0 to 100 inclusive is determined based on the input data. In some implementations the score can be normalized to cover a different range of values (e.g., 0 to 1, 0 to 1000, etc.).

The module 202 outputs a first subset of data 204 to a physical activity quality block 206. The physical activity quality block 206 determines a physical activity score 208 based on acceleration data from the sensor apparatus 110. Further details on the physical activity quality block 206 are discussed with reference to FIGS. 3-5.

The module 202 outputs a second subset of data 210 to a sleep quality block 212. The sleep block 212 determines a sleep score for the user based on sleep data from the sensor apparatus 110. For example, a sleep duration, a sleep latency, and a sleep efficiency are derived based on the sleep data. The sleep block 212 determines a sleep score based on one or more of the sleep duration, sleep latency, and sleep efficiency. Further details on the sleep quality block 212 are discussed with reference to FIG. 6.

The module 202 outputs a third subset of data 216 to a vital signs quality block 218. The vital signs quality block 218 determines a vital signs score 220 based on sensor data including a measure of one or more vital signs of the user (e.g., heart rate), acceleration data, and activity classification. The vital signs score 220 can be used to indicate the health and well-being of the user during various daily activities. By considering, for example, heart rate patterns during sleep, wake resting periods, low physical activity, and high physical activity, the vital signs score 220 provides valuable insights into the capacity of a user's physiological systems to respond appropriately to daily human activities. This ultimately facilitates a more holistic understanding of an individual's health and quality of life. Further details on the vital signs quality block 218 are discussed with reference to FIGS. 7-8.

The physical activity score 208, sleep score 214, and vital signs score 220 are combined in the overall quality of life score block 222 to determine an overall health related quality of life score for the user. For example, each of the aspect scores 208, 214, 220 are averaged to generate the overall quality of life score. The overall quality of life score can be in the range of 0 to 100 inclusive. In some implementations, the overall quality of life score can be generated using a weighted average where a weight is assigned to each of the aspect scores 208, 214, 220. Other methods of combining the aspect scores 208, 214, 220 are also possible. For example, a non-linear weighted sum can be used where a non-linear function is applied to each aspect score prior to summation, a regression model can be used to predict an overall score based on the aspect scores, or a categorical or cluster score can be determined based on overall scores associated with groupings of aspect scores.

In some implementations, the user can be monitored based on the health related quality of life score. For example, a health provider can provide recommendations (e.g., activity recommendations, behavior changes) to the user to improve their health related quality of life score.

Figure 3:
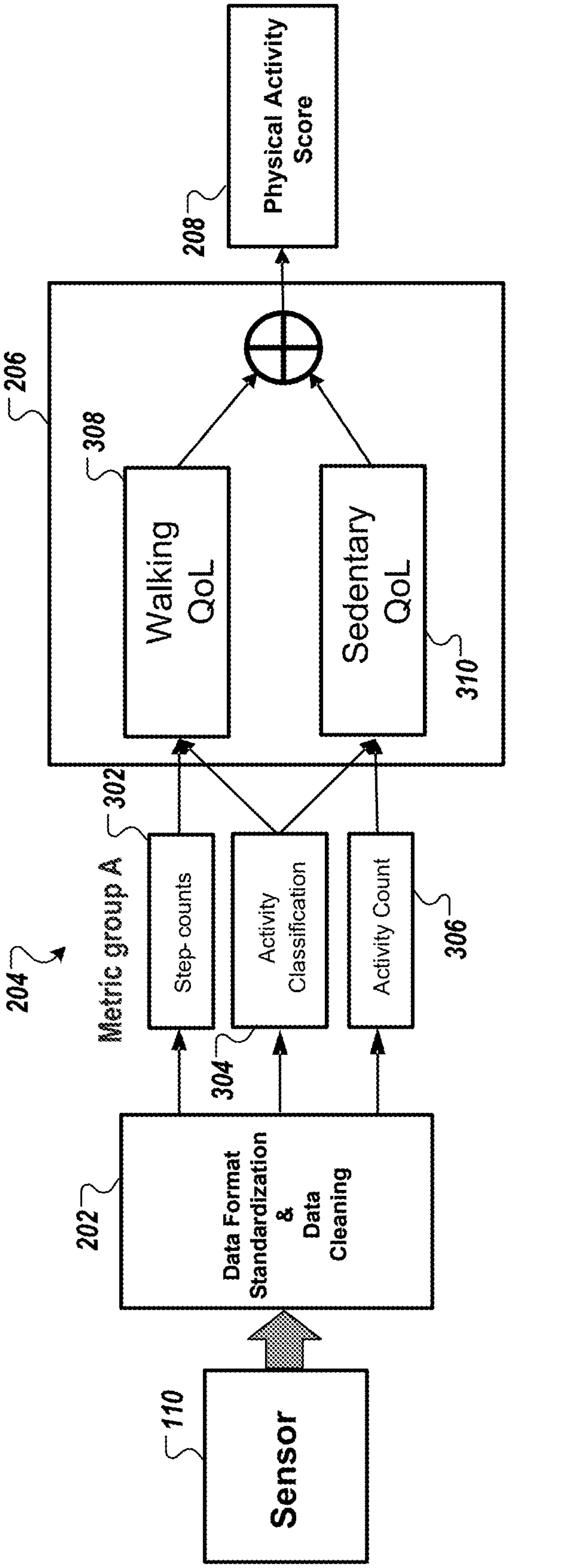
FIG. 3 is a flow chart diagram for an example method of determining a physical activity score.
Figure 4:
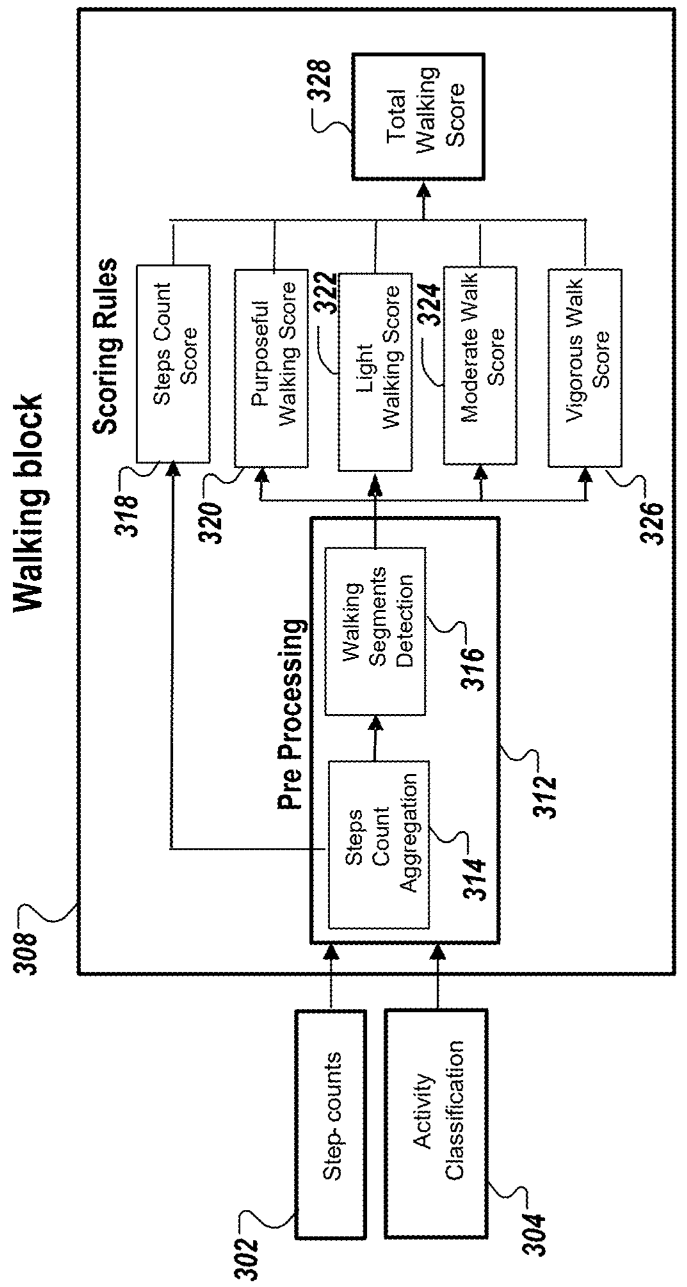
FIG. 4 is a flow chart diagram for an example method for determining a walking score.
Figure 5:
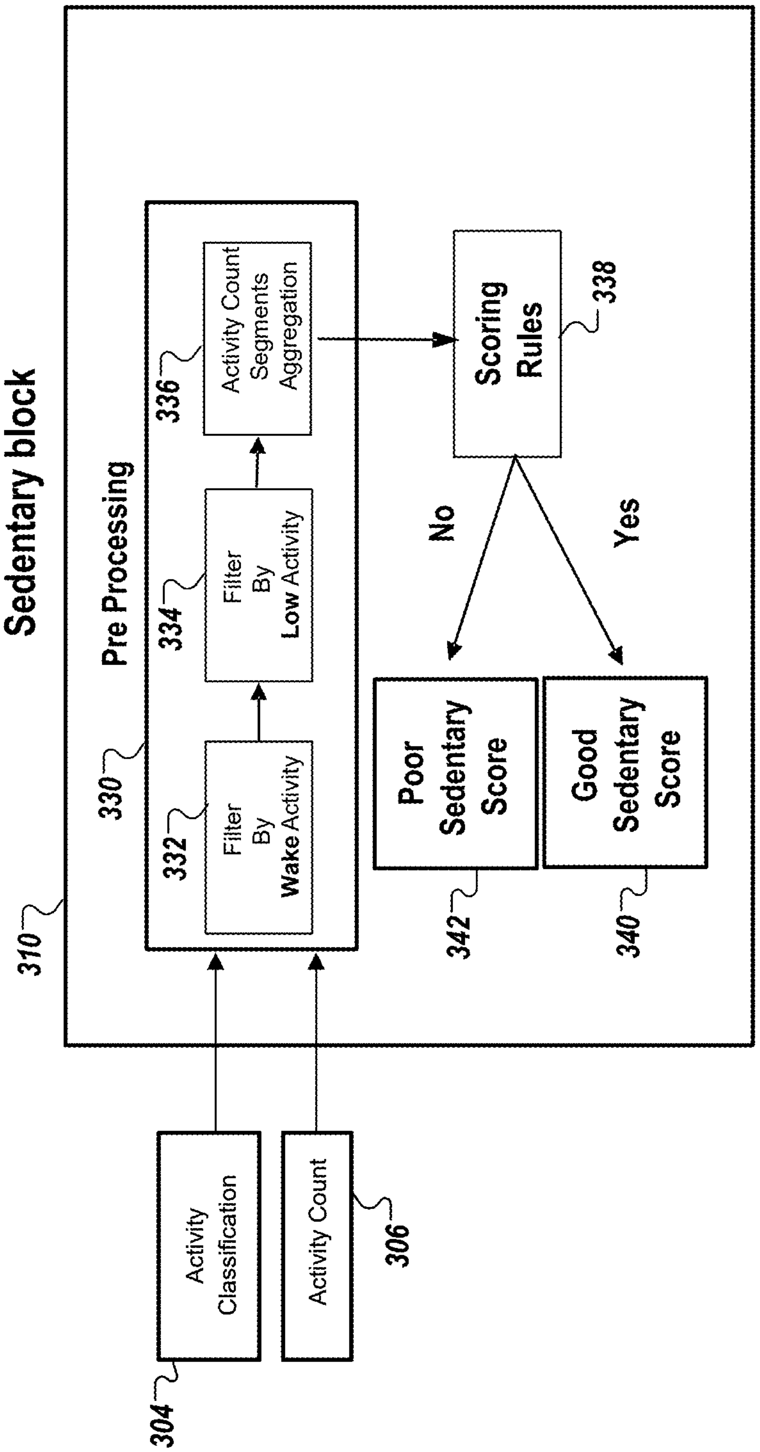
FIG. 5 is a flow chart diagram for an example method for determining a sedentary score.

FIGS. 3-5 are flow charts for example methods for determining the physical activity score 208. The physical activity quality block 206 receives as input the first subset of data 204 including step counts 302, activity classification 304, and activity count 306. The steps count 302 includes a number of steps taken by the user derived for example from acceleration data. The step counts 302 can also include a time associated with when the steps were taken to determine a rate of steps taken (e.g., steps per minute, steps per hour). The activity classification 304 includes a classification of the activity into one of multiple classes. Activity classes, for example, can include walking, sedentary, sleeping, resting, moving, sitting, leaning, standing, etc. The activity count 306 indicates an intensity of the user's physical activity. The physical activity quality block 206 uses two sub-blocks, walking quality of life 308 and sedentary quality of life 310 to determine the overall physical activity score 208. The walking quality of life block 308 provides insights on the ability of a user to walk on a daily basis, and the sedentary quality of life block 310 informs about the user's daily sedentary behavior (e.g., periods of inactivity).

The walking quality of life block 308 takes as input the steps count 302 and activity classification 304. A data preprocessing step 312 prepares the input data for input to sub-scoring blocks 318-326. The data preprocessing step 312 includes step count aggregation 314 where the step-counts are totaled over specified periods of time (e.g., an hour, a day, a week). The data processing step 312 also includes walking segment detection 316. For example, the activity classification 304 indicates periods of time when the user is walking. The walking segments detection 316 determines periods of time when the user is walking (e.g. 2, 6 or 'n' minutes of walk). The walking segments detection 316 can be used to determine rates of steps taken during the periods of time indicated as walking (e.g., steps per minute).

The sub-scoring blocks 318-326 determine walking sub-scores for the user that are combined into a total walking score 328. The steps count score 318 takes as input the total step count from the step count aggregation 314. The steps count score 318 scores the user based on the number of steps taken during a day. The steps count score 318 can correlate a certain number of daily steps to reduced risk in all-cause mortality. For example, if the steps count exceeds a threshold number of steps per day (e.g., 6,000-8,000 steps per day for a user 60 years of age or older or 8,000-10,000 steps per day for a user younger than 60 years old), the user receives a steps count score of 1. If the threshold number of steps is not exceeded, the user receives a steps count score of 0. In some implementations, if the threshold number of steps is not exceeded, the steps count score is the ratio of the number of steps taken during a day over the threshold number of steps.

The walking segments are the inputs to each of the four remaining sub-scoring blocks 320-326, which generate a sub-score according to the intensity with which a user walks each day or on a weekly basis to obtain a positive impact on their health. The purposeful walking score 320 indicates if 30 minutes of purposeful walk (e.g., walking <1 min per segment) was detected per day. If so, the user receives a purposeful walking score of 1. If not, the user receives a purposeful walking score of 0 or the ratio of the minutes of purposeful walking over the goal (e.g., 30 minutes). Purposeful steps can be filtered from incidental steps based on the rate of steps. For example, incidental steps can be considered when the number of steps taken per minute is less than 40 steps per minute, while purposeful steps can be steps taken with a rate of 40 steps per minute up to 60 steps per minute.

The light walking score 322 indicates if a threshold amount (e.g., 30 minutes) of light walking (e.g., with a duration greater than 1 min) was detected per day. A light walking intensity can include, for example, periods of time with a step rate of 60 steps per minute up to 100 steps per minute. If the threshold amount of light walking is achieved, the user can receive a 1 score, and if the threshold is not achieved, the user can receive a zero or a partial score based on the ratio of the minutes of light walk divided by the threshold.

The moderate walking score 322 and the vigorous walking score 324 indicate if the user achieved at least 10 minutes of moderate walk intensity (e.g., 100-129 steps/min) or 10 minutes of vigorous walk intensity (e.g., more than 130 steps/min) per day. For both the moderate walking score 322 and the vigorous walking score 324, the user receives a 1 score if the threshold is achieved and a zero or ratio score if the threshold is not achieved.

The sub-scores from the sub-scoring blocks 318-326 can be combined into a total walking score 328, for example, by averaging the sub-scores. In some implementations, a weighted average of the sub-scores can be used to determine the total walking score 328. For example, the steps count score 318 can receive a higher weight than other sub-scores. An example weighting scheme includes a 0.7 weight for the step count, a 0.7 weight for the purposeful walk score, a 0.7 weight for the light walk score, a 0.9 weight for the moderate walk score, and a 1 weight for the vigorous walk score. In some implementations, the total walking score 328 can be a 1 score if at least one of the sub-scores achieves a 1 score. Achieving a 1 score for any of the sub-scoring blocks could help a user reduce all cost mortality.

The sedentary quality of life block 310 considers the amount of time spent in sedentary mode (e.g., inactive, resting, sitting, etc.) outside of the user's sleep routine. The sedentary quality of life block 310 takes as input the activity classification 304 and the activity count 306. The input data is preprocessed in block 330. Preprocessing includes a filter by wake activity 332 which filters the activity count 306 by periods of activity classified as awake (e.g., not sleeping). The data is further filtered by a low activity filter 334 which identifies periods of activity with low activity counts. Sedentary behavior includes daily sitting time such as television (TV) viewing, and periods of sedentary behavior can be located at the lowest of the physical activity spectrum (or low activity count), outside of sleep time. An activity count segments aggregation 336 finds and aggregates periods of low continuous activity counts (e.g., data segments indicated as awake activity with low activity counts). The aggregated activity count segments are input into the sedentary scoring rules 338 to determine the sedentary quality of life score. The sedentary score can be determined based on the total amount of time spent in a sedentary mode by the user. For example, a threshold of 4 hours can be used to differentiate between poor or good sedentary behavior. For example, less than 4 hours of aggregated sedentary behavior can result in a good sedentary score 340 (e.g., a 1 score). Four or more hours of aggregated sedentary behavior can result in a poor sedentary score 342 (e.g., a zero score).

Each of the sub-scores 318-326, 340-342 can be determined on a binary basis (e.g., 1 for meeting or exceeding the criteria and 0 otherwise) or on a continuous scale (e.g., a ratio based on the proportion of the criteria met). A continuous score can make it easier to express the user's ability to achieve a habit considered beneficial for a good quality of life. In this way, a physical activity score 208 higher than one can be interpreted as a strong ability to perform that daily aspect. On the other hand, when the physical activity score is lower than one, this can indicate a weaker ability to perform that particular aspect.

The overall physical activity score 208, can be determined by combining the total walking score 328 with the sedentary score 340 or 342. For example, the physical activity score 208 can be a sum, average, or weighted average of the total walking score 328 and the sedentary score 340 or 342.

Figure 6:
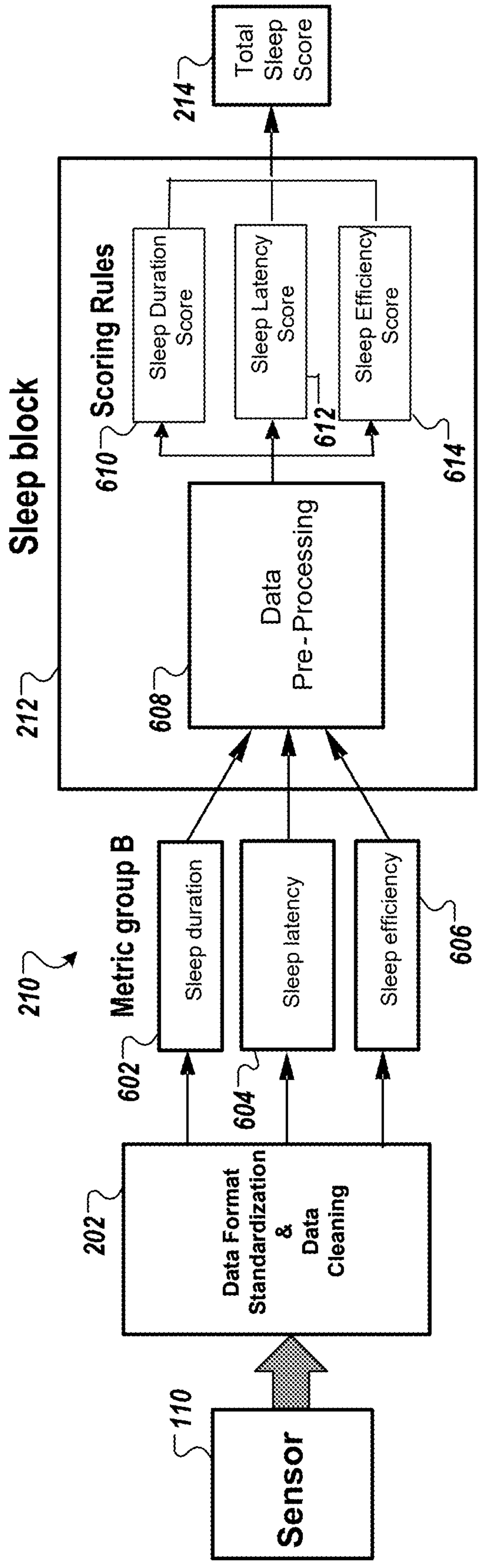
FIG. 6 is a flow chart diagram for an example method for determining a sleep score.

FIG. 6 is a flow chart of an example method for determining the total sleep score 214. The sleep block 212 takes as input a second data subset 210 from the common data and data cleaning module 202. The second data subset 210 includes sleep duration 602 (e.g., amount of time spent asleep), sleep latency 604 (e.g., amount of time after going to bed before falling asleep), and sleep efficiency 606 (e.g., amount of time in bed spent sleeping). The input data 602-606 is fed into a data pre-processing block 608. The data pre-processing block 608 can format and/or sort the input data 602-606 for input into the scoring rules 610-614.

The scoring rules 610-614 receive the data from the data preprocessing block 608. The sleep duration score 610 is based on the amount of sleep time per day. For example, if the sleep duration is 7 hours or more, the sleep duration score 610 is 0, if the sleep duration is between 6 hours and 7 hours the sleep duration score 610 is 1, between 5 hours and 6 hours the sleep duration score 610 is 2, and if the sleep duration is lower than 5 then the sleep duration score 610 is 3.

The sleep latency score 612 represents the amount of time from being in bed until the actual sleep onset of the user. For example, if sleep latency is 15 min or less, the sleep latency score 612 is 0, the sleep latency score 612 is 1 if the sleep latency is between 15 and 30 minutes, the sleep latency score 612 is 2 if the sleep latency is between 30 and 60 minutes, and the sleep latency score 612 is 3 if the sleep latency is greater than 60 minutes.

The sleep efficiency score 614 is based on the ratio between total sleep time and the total time the user is in bed. For example, the sleep efficiency score 614 is 0 if the user's sleep efficiency is 85% or more, the sleep efficiency score 614 is 1 if the sleep efficiency is between 75% and 85%, the sleep efficiency score 614 is 2 if the sleep efficiency is between 65% and 75%, and sleep efficiency score 614 is 3 if the sleep efficiency is lower than 65%.

In the preceding examples, each sleep score 610-614 is a score value ranging from 0-3, where 0 is the best score and 3 is the worst score. The total sleep score 214 can be determined as a sum of each of the sleep scores 610-614 giving a total score range between 0-9. To combine the total sleep score with the physical activity score 208 and the vital signs score 220, the total sleep score can be normalized and inverted. For example, the total sleep score 214 can be normalized to the range from 0 to 1 or 0 to 100 by dividing by the maximum possible sleep score (e.g., 9) and multiplying by the desired range. The sleep score can be inverted such that 0 is a poor sleep score and 1 or 100 is a good sleep score by, for example, subtracting the normalized score from the maximum score in the desired range.

Figure 7:
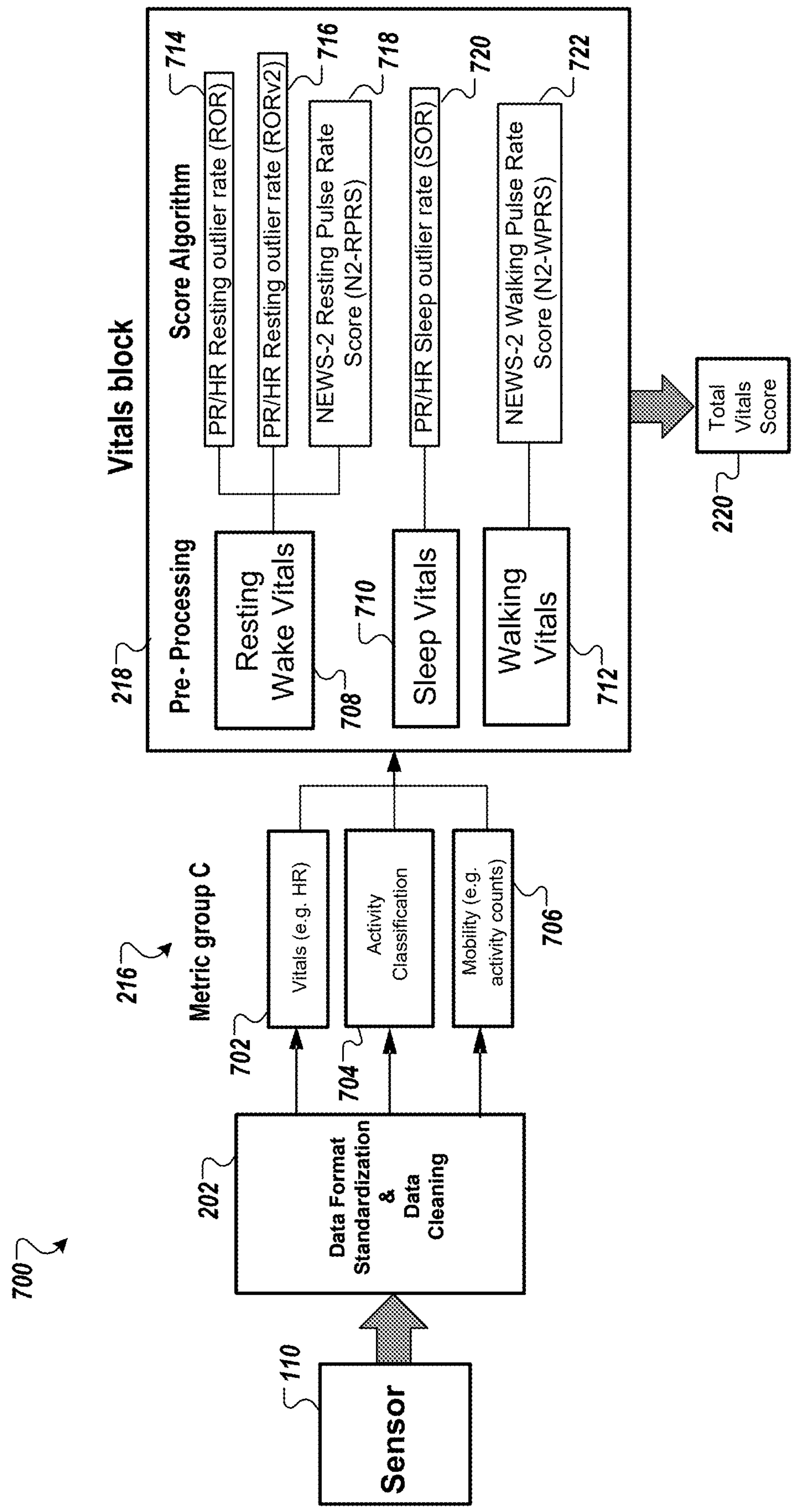
FIG. 7 is a flow chart diagram for an example method for determining a vital signs score.

FIG. 7 is a flow chart for an example method 700 for determining a vital signs score. The vital signs quality block 218 takes as input the third data subset 216 from the data format standardization and data cleaning module 202. The third data subset 216 includes vital sign metrics 702 (e.g., heart rate, respiration rate, blood oxygen level), activity classification 704, and activity counts 706. The vital signs quality block 218 identifies if a user's vital signs are responding as expected given a particular daily activity. The input data is preprocessed (e.g., filtered, sorted) based on three activity categories, which include resting wake vitals 708, sleeping vitals 710, and walking vitals 712. For example, the data vital sign metrics 702 are sorted based on activity classification 704 and activity counts 706. After preprocessing, the vitals 708-712 are scored based on various criteria.

The pulse rate/heart rate (PR/HR) resting outliers rate 714 (ROR) indicates the percentage of HR samples outside "normal" ranges during resting time. For this score, periods of PR/HR within the "normal" range and outside the normal range are aggregated. The percentage of outliers is determined based on comparing the samples that were within the normal range. The second version of the PR/HR resting outliers rate 716 (RORv2) takes into account continuous resting periods (e.g., resting periods greater than 5 minutes). For both scores 714-716, the score can be between 0% and 100%, where the best possible outcome is represented by 100 (e.g., when the outlier rate is 0) and the worst is represented by 0 (when the outliers rate is 100).

The PR/HR sleep outliers rate 720 (SOR) can be determined similarly to ROR and RORv2 scores. In the case of SOR 720, the "normal" range for heart rate is shifted to ranges appropriate for sleeping. For example, a "normal" range for a sleeping heart rate can be 20% to 30% below a resting heart rate for a typical adult. A typical resting heart rate can be, for example, 50-70 beats per minute. In some implementations, the range can be personalized for the user (e.g., based on the user's historical heart rate values).

Two additional scores 718, 722 are based on the National Early Warning Score (NEWS) framework to determine users at risk of developing sepsis given their vital signs (e.g., to detect whether the user's organs are working poorly). In this framework, higher scores are indicative of a more severe illness and a greater need for immediate medical intervention. For example, in the NEWS-2 Resting PR/HR Score 718, resting vitals segments are determined and scored for each day. For example, if any beats per minute (bpm) sample is between 51-90 the score is zero (or normal), the score is 1 if the bpm sample is between 41-50 bpm or 91-110 bpm, the score is 2 if the bpm sample is between 111-130 bpm, and the score is 3 if the bpm sample is lower than 40 bpm or greater than 130 bpm. For each segment, two example options for determining the overall resting segment score include determining the average score of the resting segment, and determining the score based on the maximum score from the resting segment (indicating worst condition during the segment). The overall daily score can be determined using the same options, e.g., average score or maximum score. Use of the maximum score can be a more cautious approach.

For the NEWS-2 Walking PR/HR Score 722, the process looks similar as described for the NEWS-2 Resting PR/HR Score 718 with the ranges for each score shifted based on personalized user baseline offset adjustments. When determining the HR/PR score during walking (or any form of exercise), the ranges for normal or abnormal vitals established in the raw National Early Warning Score (NEWS-2) do not apply, as these were established only for resting HR/PR. A user baseline resting heart rate is, for example, the average value between the 25th and 75th percentiles (interquartile range or IQR) which captures the middle 50% of the data and is a good measure for the typical variation in a person's heart rate. For each walking segment detected during the day, the median walking HR is calculated. From these two values, a difference variable is determined as the difference between the median and the baseline walking heart rate. This difference is added to each of the values of the NEWS-2 ranges described before, and the process for a final daily score works as described for the NEWS-2 Resting PR/HR score 718.

The total vitals score 220 can be determined based on a sum, average, or weighted average of the various scores 714-722. For example, the total vitals score 220 can be a value between 0 and 1 or 0 and 100 indicating the average value of the sores 714-722, which themselves are values between 0 and 1 or 0 and 100.

Figure 8:
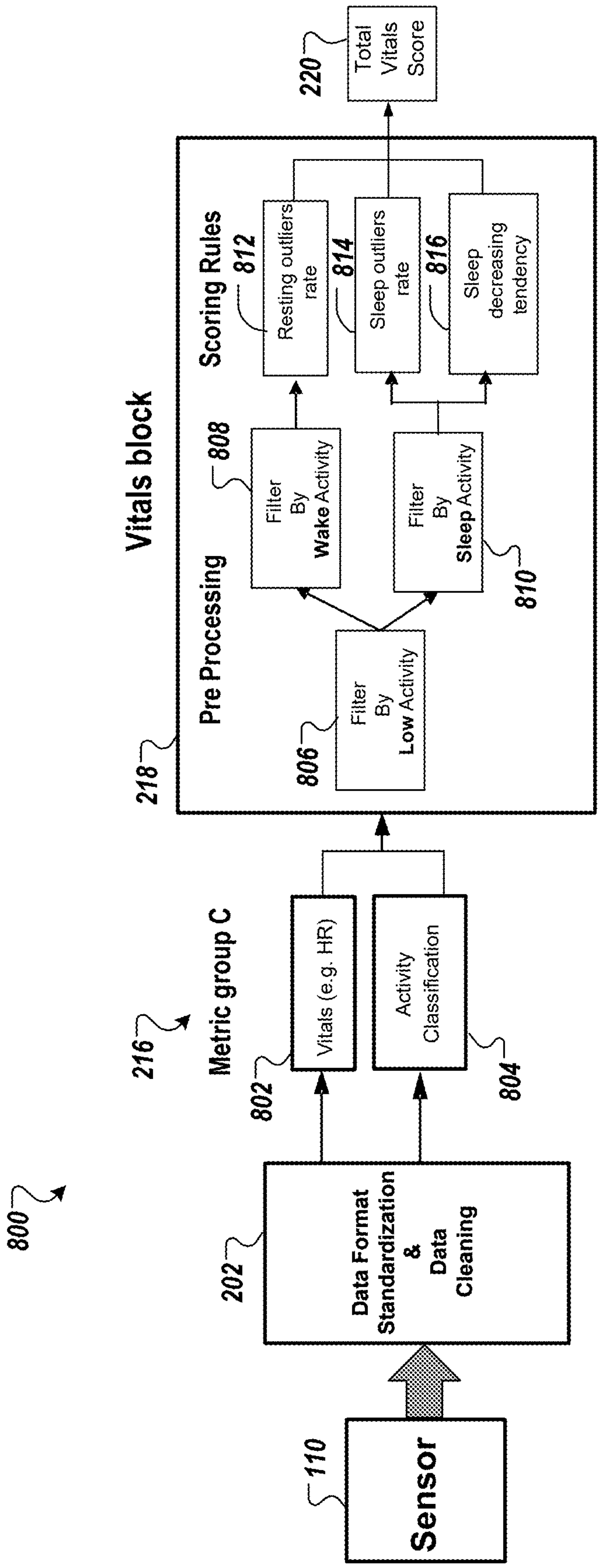
FIG. 8 is a flow chart diagram for another example method for determining a vital signs score.

FIG. 8 is a flow chart for another example method 800 for determining a vital signs score 220. The vital signs quality block 218 takes as input the vital signs 802 and activity classification 804 output from the common data model and data cleaning module 202.

The vital signs 802 are filtered into low activity segments based on the activity classification 804. For example, the vital signs 802 are filtered based on sedentary, resting, and/or sleeping activity classes. The vital signs 802 are further sorted into wake activity 808 and sleep activity 810 based on the activity classification 804.

The wake activity 808 is scored based on a resting outlier rate 812. For this score periods of PR/HR within the "normal" range and outside the normal range are aggregated. The percentage of outliers is determined based on comparing the samples that were within the normal range (e.g., identifying samples that deviate more than a threshold value from the mean value of the HR in the normal range). The resting outlier rate 812 can be expressed as a number between 0 and 1 or 0 and 100 indicating the percentage of data sample identified as outliers.

The sleep outlier rate 814 is based on the sleep activity 810. Similar to the resting outlier rate 812, the sleep outlier rate 814 scores periods of PR/HR with normal sleeping ranges and outside normal sleeping ranges. The sleep outlier rate 814 can be expressed as a number between 0 and 1 or 0 and 100 indicating the percentage of sleep activity identified as outliers.

The sleep activity 810 is additionally scored to determine a sleep decreasing tendency 816. The sleep decreasing tendency 816 can measure the trend of heart rate decrease while sleeping. In some implementations, the sleep decreasing tendency can have a shape similar to a f (x)=1/$x^2$ line with an asymptote at 20-30% of the subject's resting heart rate.

Example Processes

Figure 9:
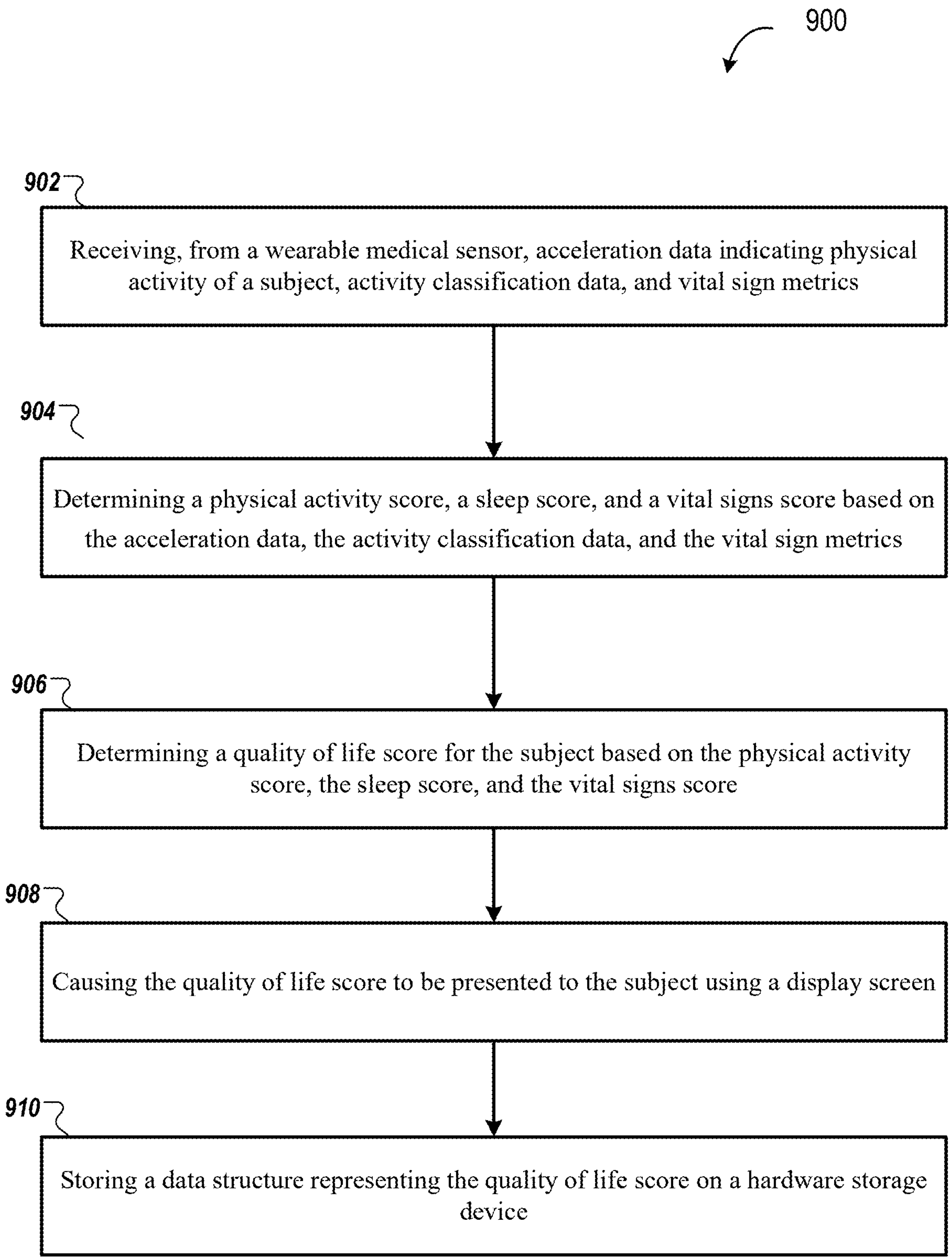
FIG. 9 is a flow chart diagram of an example process for monitoring a user's physical health related quality of life.

FIG. 9 shows an example process 900 for monitoring a user's health condition using physiological sensors. In some implementations, the process 900 can be performed by the medical monitoring system 100 described in this disclosure.

In the process 900, a system receives 902 acceleration data indicating physical activity of a subject, activity classification data, and vital sign metrics from a wearable medical sensor. The system determines 904 a physical activity score, a sleep score, and a vital signs score based on the acceleration data, the activity classification data, and the vital sign metrics. The system determines 906 a quality of life score for the subject based on the physical activity score, the sleep score, and the vital signs score. The system causes 908 the quality of life score to be presented to the subject using a display screen. The system stores 910 a data structure representing the quality of life score on a hardware storage device.

In some implementations, the system determines that the quality of life score is less than a threshold quality of life score; and in response to determining that the quality of life score is less than the threshold quality of life score, the system causes an alert to be generated indicating that the quality of life score is less than the threshold quality of life score.

In some implementations, the system receives heart rate data and data specifying a steps count from the wearable medical sensor, where the vital signs score is determined based on the heart rate data, the steps count, and the activity classification data.

In some implementations, determining the vital signs score includes receiving sleep metrics from the wearable medical sensor; determining a resting while awake vitals score based on the activity classification data, the acceleration data, and the heart rate data; determining a sleeping vitals score based on the activity classification data, the acceleration data, sleep metrics, and the heart rate data; determining a walking vitals score based on the activity classification data, the acceleration data, the steps count and the heart rate data; and determining the vital signs score based on the resting while awake vitals score, the sleeping vitals score, and the walking vitals score.

In some implementations, determining the physical activity score includes determining a walking score and a sedentary score.

In some implementations, the system receives data specifying a steps count from the wearable medical sensor, where the walking score is determined based on the steps count, the acceleration data, and the activity classification data; and the sedentary score is determined based on the activity classification data and an activity count based on the acceleration data.

In some implementations, the activity count represents movement of the subject determined based on a magnitude of the acceleration over a time interval.

In some implementations, the system filters the activity classification data to extract low activity samples while the subject is awake, where the sedentary score includes a count of continuous low activity samples while the subject is awake.

In some implementations, the walking score includes a step count score, a purposeful walk score, a light walk score, a moderate walk score, and a vigorous walk score, where each of the purposeful walk score, the light walk score, the moderate walk score, and the vigorous walk score is determined based on a number of steps in a time interval.

In some implementations, determining the sleep score includes determining one or more of a sleep duration score, a sleep latency score, and a sleep efficiency score based on the sleep metrics.

In some implementations, the system determines, based on the quality of life score, one or more recommendations for improving a health of the subject, and causes the one or more recommendations to be presented to the subject.

Example Computer Systems

Figure 10:
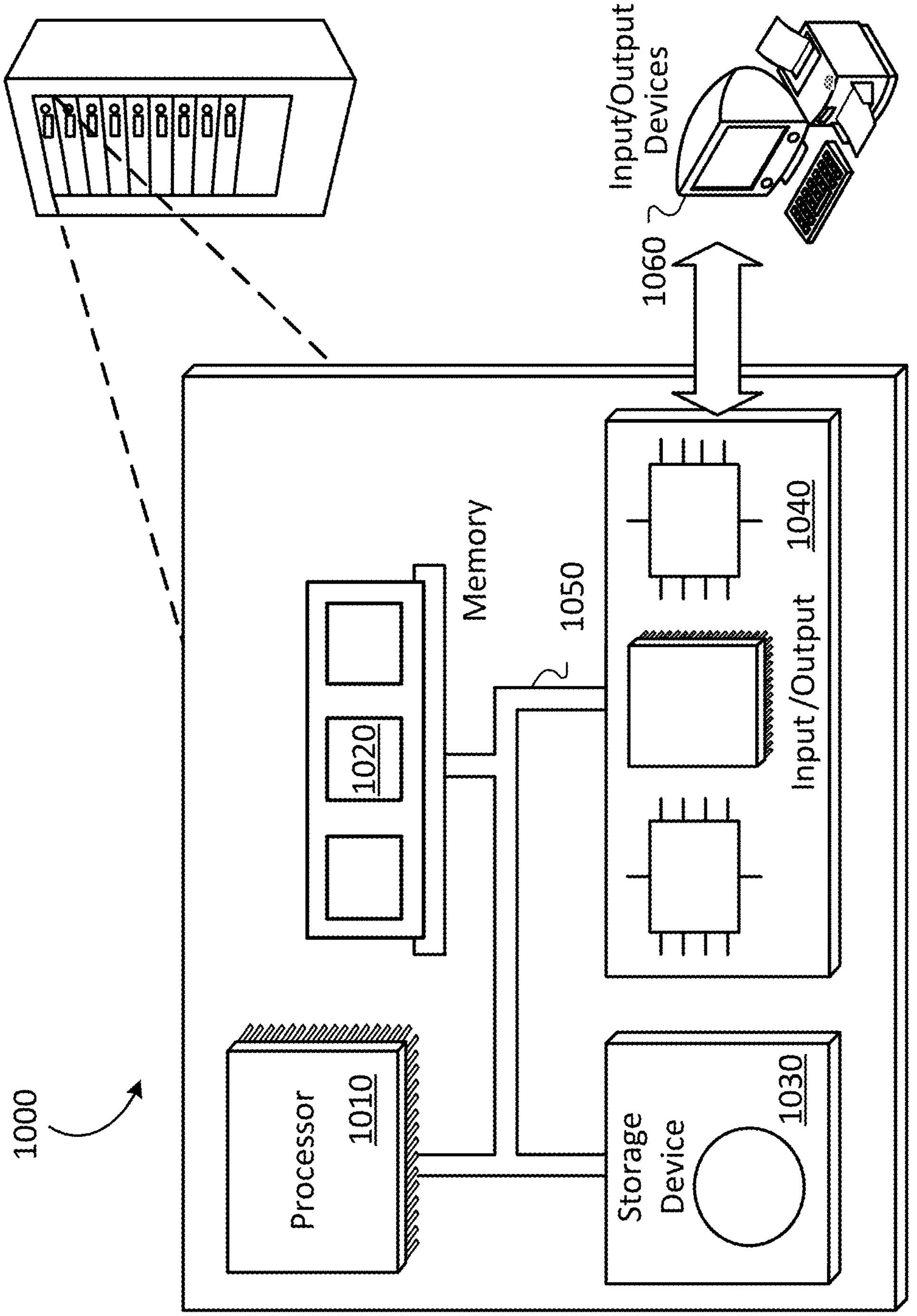
FIG. 10 is a diagram of an example computer system.

FIG. 10 depicts an example computing system, according to implementations of the present disclosure. The system 1000 may be used for any of the operations described with respect to the various implementations discussed herein. The system 1000 may include one or more processors 1010, a memory 1020, one or more hardware storage devices 1030, and one or more input/output (I/O) devices 1060 controllable through one or more I/O interfaces 1040. The various components 1010, 1020, 1030, 1040, or 1060 may be interconnected through at least one system bus 1050, which may enable the transfer of data between the various modules and components of the system 1000.

The processor(s) 1010 may be configured to process instructions for execution within the system 1000. The processor(s) 1010 may include single-threaded processor(s), multi-threaded processor(s), or both. The processor(s) 1010 may be configured to process instructions stored in the memory 1020 or on the storage device(s) 1030. The processor(s) 1010 may include hardware-based processor(s) each including one or more cores. The processor(s) 1010 may include general purpose processor(s), special purpose processor(s), or both.

The memory 1020 may store information within the system 1000. In some implementations, the memory 1020 includes one or more computer-readable media. The memory 1020 may include any number of volatile memory units, any number of non-volatile memory units, or both volatile and non-volatile memory units. The memory 1020 may include read-only memory, random access memory, or both. In some examples, the memory 1020 may be employed as active or physical memory by one or more executing software modules.

The storage device(s) 1030 may be configured to provide (e.g., persistent) mass storage for the system 1000. In some implementations, the storage device(s) 1030 may include one or more computer-readable media. For example, the storage device(s) 1030 may include a floppy disk device, a hard disk device, an optical disk device, or a tape device. The storage device(s) 1030 may include read-only memory, random access memory, or both. The storage device(s) 1030 may include one or more of an internal hard drive, an external hard drive, or a removable drive.

One or both of the memory 1020 or the storage device(s) 1030 may include one or more computer-readable storage media (CRSM). The CRSM may include one or more of an electronic storage medium, a magnetic storage medium, an optical storage medium, a magneto-optical storage medium, a quantum storage medium, a mechanical computer storage medium, and so forth. The CRSM may provide storage of computer-readable instructions describing data structures, processes, applications, programs, other modules, or other data for the operation of the system 1000. In some implementations, the CRSM may include a data store that provides storage of computer-readable instructions or other information in a non-transitory format. The CRSM may be incorporated into the system 1000 or may be external with respect to the system 1000. The CRSM may include read-only memory, random access memory, or both. One or more CRSM suitable for tangibly embodying computer program instructions and data may include any type of non-volatile memory, including but not limited to: semiconductor memory devices, such as EPROM, EEPROM, and flash memory devices; magnetic disks such as internal hard disks and removable disks; magneto-optical disks; and CD-ROM and DVD-ROM disks. In some examples, the processor(s) 1010 and the memory 1020 may be supplemented by, or incorporated into, one or more application-specific integrated circuits (ASICs).

The system 1000 may include one or more I/O devices 1060. The I/O device(s) 1060 may include one or more input devices such as a keyboard, a mouse, a pen, a game controller, a touch input device, an audio input device (e.g., a microphone), a gestural input device, a haptic input device, an image or video capture device (e.g., a camera), or other devices. In some examples, the I/O device(s) 1060 may also include one or more output devices such as a display, LED(s), an audio output device (e.g., a speaker), a printer, a haptic output device, and so forth. The I/O device(s) 1060 may be physically incorporated into one or more computing devices of the system 1000, or may be external with respect to one or more computing devices of the system 1000.

The system 1000 may include one or more I/O interfaces 1040 to enable components or modules of the system 1000 to control, interface with, or otherwise communicate with the I/O device(s) 1060. The I/O interface(s) 1040 may enable information to be transferred in or out of the system 1000, or between components of the system 1000, through serial communication, parallel communication, or other types of communication. For example, the I/O interface(s) 1040 may comply with a version of the RS-232 standard for serial ports, or with a version of the IEEE 1284 standard for parallel ports. As another example, the I/O interface(s) 1040 may be configured to provide a connection over Universal Serial Bus (USB) or Ethernet. In some examples, the I/O interface(s) 1040 may be configured to provide a serial connection that is compliant with a version of the IEEE 1394 standard.

The I/O interface(s) 1040 may also include one or more network interfaces that enable communications between computing devices in the system 1000, or between the system 1000 and other network-connected computing systems. The network interface(s) may include one or more network interface controllers (NICs) or other types of transceiver devices configured to send and receive communications over one or more networks using any network protocol.

Computing devices of the system 1000 may communicate with one another, or with other computing devices, using one or more networks. Such networks may include public networks such as the internet, private networks such as an institutional or personal intranet, or any combination of private and public networks. The networks may include any type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In some implementations, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

The system 1000 may include any number of computing devices of any type. The computing device(s) may include, but are not limited to: a personal computer, a smartphone, a tablet computer, a wearable computer, an implanted computer, a mobile gaming device, an electronic book reader, an automotive computer, a desktop computer, a laptop computer, a notebook computer, a game console, a home entertainment device, a network computer, a server computer, a mainframe computer, a distributed computing device (e.g., a cloud computing device), a microcomputer, a system on a chip (SoC), a system in a package (SiP), and so forth. Although examples herein may describe computing device(s) as physical device(s), implementations are not so limited. In some examples, a computing device may include one or more of a virtual computing environment, a hypervisor, an emulation, or a virtual machine executing on one or more physical computing devices. In some examples, two or more computing devices may include a cluster, cloud, farm, or other grouping of multiple devices that coordinate operations to provide load balancing, failover support, parallel processing capabilities, shared storage resources, shared networking capabilities, or other aspects.

This specification uses the term "configured" in connection with systems and computer program components. For a system of one or more computers to be configured to perform particular operations or actions means that the system has installed on software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively, or in addition, the program instructions can be encoded on an artificially generated propagated signal, e.g., a machine-generated electrical, optical, or electromagnetic signal, that is generated to encode information for transmission to a suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially be claimed as such, one or more features from a claimed combination can in some cases be excised from the combination, and the claimed combination may be directed to a sub combination or variation of a sub combination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A medical system comprising:

a wearable medical sensor comprising an accelerometer and a vital signs sensor;

a display screen;

a hardware storage device; and at least one processor and a memory storing instructions that when executed by the at least one processor cause performance of operations comprising:

receiving, from the accelerometer of the wearable medical sensor, acceleration data indicating physical activity of a subject;

receiving, from the wearable medical sensor, activity classification data and sleep data, wherein the activity classification data classifies the physical activity indicated by the acceleration data received from the accelerometer to more than two classes based on one or more characteristics of the physical activity;

receiving, from the vital signs sensor, one or more vital sign metrics;

based on the received activity classification data that classifies the physical activity indicated by the acceleration data received from the accelerometer to the more than two classes based on the one or more characteristics of the physical activity, classifying the one or more vital sign metrics to a class of the more than two classes to which the physical activity indicated by the acceleration data received from the accelerometer is classified;

determining a physical activity score, a sleep score, and a vital signs score based on the acceleration data, the activity classification data, the sleep data, and the one or more vital sign metrics, wherein the vital signs score is at least partly based on the classifying of the one or more vital sign metrics to the class to which the physical activity indicated by the acceleration data received from the accelerometer is classified;

determining a quality of life score for the subject based on the physical activity score, the sleep score, and the vital signs score;

causing a visual representation of the quality of life score to be rendered on the display screen;

determining, based on the quality of life score, one or more recommendations for improving a health of the subject; and causing the one or more recommendations to be presented to the subject.

2. The medical system of claim 1, wherein the operations further comprise:

determining that the quality of life score is less than a threshold quality of life score; and in response to determining that the quality of life score is less than the threshold quality of life score, causing an alert to be generated indicating that the quality of life score is less than the threshold quality of life score.

3. The medical system of claim 1, wherein the operations further comprise:

determining a plurality of quality of life scores for the user at a plurality of times;

determining a variability in quality of life for the user based on the plurality of quality of life scores.

4. The medical system of claim 3 wherein the instructions further comprise:

determining a baseline quality of life for the user based on the plurality of quality of life scores;

determining one or more subsequent quality of life scores after determining the baseline quality of life; and determining that the one or more subsequent quality of life scores deviates more than a threshold amount from the baseline quality of life.

5. The medical system of claim 1, wherein the vital sign sensor comprises at least one of a heart rate sensor or a pulse rate sensor; and wherein the operations further comprise receiving heart rate data and data specifying a steps count from the wearable medical sensor, wherein the vital signs score is determined based on the heart rate data, the steps count, and the activity classification data.

6. The medical system of claim 5, wherein determining the vital signs score comprises:

receiving sleep metrics from the wearable medical sensor;

determining a resting while awake vitals score based on the activity classification data, the acceleration data, and the heart rate data;

determining a sleeping vitals score based on the activity classification data, the acceleration data, the sleep metrics, and the heart rate data;

determining a walking vitals score based on the activity classification data, the acceleration data, the steps count and the heart rate data; and determining the vital signs score based on the resting while awake vitals score, the sleeping vitals score, and the walking vitals score.

7. The medical system of claim 1, wherein determining the physical activity score comprises determining a walking score and a sedentary score.

8. The medical system of claim 7, wherein the operations further comprise:

receiving data specifying a steps count from the wearable medical sensor, wherein the walking score is determined based on the steps count, the acceleration data, and the activity classification data; and the sedentary score is determined based on the activity classification data and an activity count based on the acceleration data.

9. The medical system of claim 8, wherein the activity count represents movement of the user determined based on a magnitude of the acceleration over a time interval.

10. The medical system of claim 9, wherein the operations further comprise:

filtering the activity classification data to extract low activity samples while the user is awake, wherein the sedentary score comprises a count of continuous low activity samples while the user is awake.

11. The medical system of claim 8, wherein the walking score comprises:

a step count score, a first walk score indicative of as step rate above a first threshold and below a second threshold, a second walk score indicative of a step rate less than a third threshold, a third walk score indicative of a step rate above a fourth threshold, and a fourth walk score indicative of a step rate above a fifth threshold, wherein each of the first walk score, the second walk score, the third walk score, and the fourth walk score is determined based on a number of steps in a time interval.

12. The medical system of claim 6, wherein determining the sleep score comprises determining one or more of a sleep duration score, a sleep latency score, and a sleep efficiency score based on the sleep metrics.

13. A method for determining a quality of life of a user, the method comprising:

receiving, from an accelerometer of a wearable medical sensor, acceleration data indicating physical activity of a user;

receiving, from the wearable medical sensor, activity classification data and sleep data, wherein the activity classification data classifies the physical activity indicated by the acceleration data received from the accelerometer to more than two classes based on one or more characteristics of the physical activity;

receiving, from a vital signs sensor of the wearable medical senor, one or more vital sign metrics;

based on the received activity classification data that classifies the physical activity indicated by the acceleration data received from the accelerometer to the more than two classes based on the one or more characteristics of the physical activity, classifying the one or more vital sign metrics to a class of the more than two classes to which the physical activity indicated by the acceleration data received from the accelerometer is classified;

determining a physical activity score, a sleep score, and a vital signs score based on the acceleration data, the activity classification data, the sleep data, and the one or more vital sign metrics, wherein the vital signs score is at least partly based on the classifying of the one or more vital sign metrics to the class to which the physical activity indicated by the acceleration data received from the accelerometer is classified;

determining a quality of life score for the user based on the physical activity score, the sleep score, and the vital signs score; and causing a visual representation of the quality of life score to be presented to the user using a display screen;

determining, based on the quality of life score, one or more recommendations for improving a health of the subject; and causing the one or more recommendations to be presented to the subject.

14. The method of claim 13 further comprising monitoring the user based on the quality of life score.

15. The method of claim 13, further comprising:

determining that the quality of life score is less than a threshold quality of life score; and in response to determining that the quality of life score is less than the threshold quality of life score, causing an alert to be generated indicating that the quality of life score is less than the threshold quality of life score.

16. The method of claim 13, further comprising receiving heart rate data and data specifying a steps count from the wearable medical sensor, wherein the vital signs score is determined based on the heart rate data, the steps count, and the activity classification data.

17. The method of claim 16, wherein determining the vital signs score comprises:

receiving sleep metrics from the wearable medical sensor;

determining a resting while awake vitals score based on the activity classification data, the acceleration data, and the heart rate data;

determining a sleeping vitals score based on the activity classification data, the acceleration data, sleep metrics, and the heart rate data;

determining a walking vitals score based on the activity classification data, the acceleration data, the steps count and the heart rate data; and determining the vital signs score based on the resting while awake vitals score, the sleeping vitals score, and the walking vitals score.

18. The method of claim 13, wherein determining the physical activity score comprises determining a walking score and a sedentary score.

19. The method of claim 18, further comprising:

receiving data specifying a steps count from the wearable medical sensor, wherein the walking score is determined based on the steps count, the acceleration data, and the activity classification data; and the sedentary score is determined based on the activity classification data and an activity count based on the acceleration data.

20. The method of claim 19, wherein the activity count represents movement of the user determined based on a magnitude of the acceleration over a time interval.

21. The method of claim 20, further comprising:

filtering the activity classification data to extract low activity samples while the user is awake, wherein the sedentary score comprises a count of continuous low activity samples while the user is awake.

22. The method of claim 19, wherein the walking score comprises:

a step count score, a purposeful walk score, a light walk score, a moderate walk score, and a vigorous walk score, wherein each of the purposeful walk score, the light walk score, the moderate walk score, and the vigorous walk score is determined based on a number of steps in a time interval.

23. The method of claim 17, wherein determining the sleep score comprises determining one or more of a sleep duration score, a sleep latency score, and a sleep efficiency score based on the sleep metrics.

24. The method of claim 13, further comprising:

determining, based on the quality of life score, one or more recommendations for improving a health of the user, and causing the one or more recommendations to be presented to the user.

25. One or more non-transitory, computer readable storage media storing instructions which, when executed by at least one processor cause the at least one processor to perform the method of claim 13.

* * * * *